(12) United States Patent
Long et al.

(10) Patent No.: US 6,630,153 B2
(45) Date of Patent: Oct. 7, 2003

(54) MANUFACTURE OF BONE GRAFT SUBSTITUTES

(75) Inventors: Marc Long, Memphis, TN (US); Michael B. Cooper, Memphis, TN (US); Keith M. Kinnane, Bartlett, TN (US); Trevor Allen, York (GB); Jeff Schryver, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/792,681

(22) Filed: Feb. 23, 2001

(65) Prior Publication Data

US 2002/0160032 A1 Oct. 31, 2002

(51) Int. Cl.$^7$ .............................. A61F 13/00; A61F 2/00; A61K 9/14; A61K 9/50
(52) U.S. Cl. ...................... 424/422; 424/423; 424/426; 424/484; 424/501
(58) Field of Search ................................. 424/422, 426, 424/484, 423, 501

(56) References Cited

U.S. PATENT DOCUMENTS

| 5,366,507 | A | | 11/1994 | Sottosanti |
| 5,569,308 | A | | 10/1996 | Sottosanti |
| 5,614,206 | A | * | 3/1997 | Randolph et al. ............ 424/426 |
| 5,626,861 | A | * | 5/1997 | Laurencin et al. ........... 424/426 |
| 5,807,567 | A | | 9/1998 | Randolph et al. |
| 5,981,828 | A | * | 11/1999 | Nelson et al. ................. 623/16 |
| 6,030,636 | A | | 2/2000 | Randolph et al. |
| 6,187,046 | B1 | * | 2/2001 | Yamamoto et al. ....... 623/16.11 |

OTHER PUBLICATIONS

*Bone grafts & bone substitutes,* Orthopedic Network News, Oct. 2000, pp. 8–10, vol. 11, No. 4, Mendenhall Associates, Inc.
*Bone graft & orthobiologicals,* Orthopedic Industry, Sep. 15, 2000, pp. 66–81, Merrill Lynch.
*iii. Bone Substitute Materials,* Executive Summary #RP–591149, 2000, pp. ES–15—ES25 & 3–1—3–45; Medical Data Int'l, Inc.

* cited by examiner

*Primary Examiner*—Thurman K. Page
*Assistant Examiner*—Blessing Fubara
(74) *Attorney, Agent, or Firm*—Fulbright & Jaworski LLP (57) ABSTRACT

The present invention is directed to methods and compositions for manufacturing a bone graft substitute. A powder compaction process is utilized to generate a shaped product comprised of a granulated bone material, such as demineralized bone matrix. In addition, a processing aid is utilized to facilitate compaction of the granulated bone material and for release of the product from the die.

33 Claims, 6 Drawing Sheets

MANUFACTURE OF BONE GRAFT SUBSTITUTES

FIELD OF THE INVENTION

The present invention is directed to compositions and methods for making bone graft substitutes. More specifically, the present invention is directed to manufacturing a bone graft substitute (BGS) by powder compaction.

BACKGROUND OF THE INVENTION

Bone graft is used to fill spaces in bone tissue that are the result of trauma, disease degeneration or other loss of tissue. Clinicians perform bone graft procedures for a variety of reasons, often to fill a bone void created by a loss of bone or compaction of cancellous bone. In many instances, the clinician also must rely on the bone graft material to provide some mechanical support, as in the case of subchondral bone replacement or compaction grafting around total joint replacement devices. In these instances, clinicians pack the material into the defect to create a stable platform to support the surrounding tissue and hardware.

There are several options available to the orthopaedic clinician for bone graft material. Most commonly, the source of the graft material is either the patient (autograft), which is clinically preferable, or a donor (allograft). However, autograft has the potential drawback of increased pain and morbidity associated with a second surgical procedure, in addition to having a limited supply of the bone. In autograft and, to a lesser extent, in allograft there are biological factors such as proteins or cells that are present that can assist in the fracture healing process. Xenografts and bone graft substitutes are other options.

Moreover, synthetically derived substitute material has advantages over human derived bone graft and naturally derived substitutes, including: 1) more control over product consistency; 2) less risk for infection and disease; 3) no morbidity or pain caused by harvesting of the patient's own bone for graft; and 4) availability of the substitute in many different volumes (that is, it is not limited by harvest site of the patient).

The BGS materials that have been used commercially exhibit various levels of bioactivity and various rates of dissolution. BGS products are currently available in several forms: powder, gel, slurry/putty, tablet, chips, morsels, and pellet, in addition to shaped products (sticks, sheets, and blocks). In many instances, the form of BGS products is dictated by the material from which they are made. Synthetic materials (such as calcium sulfates or calcium phosphates) have been processed into several shapes (tablets, beads, pellets, sticks, sheets, and blocks) and may contain additives such as antibiotics (e.g., Osteoset®-T (Wright Medical Technology; Arlington, Tenn.)) or bioactive agents (e.g., Rhakoss® (Orthovita®; Malvern, Pa.)). Allograft products, in which the source of the bone graft material is a donor, are typically available as chips and can be mixed with a gel to form a composite gel or putty. None of the current products and technologies offered for BGS is capable of offering an allograft granule or shape for easy delivery and scaffold structure, in addition to being conformable to the surgical site. Furthermore, none but one (Osteoset®-T) of the current products and technologies offered for BGS is capable of offering an allograft or synthetic granule or shape containing a bioactive agent or agents, such as an antibiotic or bone morphogenetic proteins.

Past solutions to produce BGS products have included gel, putty, paste, formable strips, blocks, granules, chips, pellets, tablets, and powder. A skilled artisan recognizes there are multiple references directed to bone graft substitutes, including *Medica Data International, Inc.*, Report #RP-591149, Chapter 3: Applications for Bone Replacement Biomaterials and Biological Bone Growth Factors (2000) and *Orthopaedic Network News*, Vol. 11, No 4, October 2000, pp. 8–10.

To date, DBM products have been produced in chips, granules, gel, or putty forms only. No solid DBM product (as opposed to a putty) which has undergone a shaping process is currently available to the health care provider. It is a disadvantage of the presently available products to have no shape which is interlocking, and the irregularly-shaped chips of presently available products do not compact sufficiently and also fail to generate reproducible results. Other calcium sulfate-based products have been made using a casting or molding process, as opposed to a dry powder compaction process of the present invention. Osteoset®-T pellets are likely to have been tableted because of their simple shape. A more complicated shape that could provide improved interlocking between the granules over the tableting process used in the art requires the use of a more advanced manufacturing process. The manufacturing of JAX™ (Smith+Nephew, Inc.; Memphis, Tenn.) bone void filler requires the use of a powder compaction process to be able to produce the advanced interlocking granule shape.

U.S. Pat. Nos. 6,030,636; 5,807,567; and 5,614,206 are directed to calcium sulfate controlled release matrix. They provide forming a pellet prepared by the process comprising mixing powder consisting essentially of alpha-calcium sulfate hemihydrate, a solution comprising water, and, optionally, an additive and a powder consisting essentially of beta-calcium sulfate hemihydrate to form a mixture, and forming the mixture into the pellet. The pellets were formed by pouring a slurry mixture of the desired components into cylindrical molds.

U.S. Pat. Nos. 5,569,308 and 5,366,507 regard methods for use in bone tissue regeneration utilizing a conventional graft material/barrier material layered scheme. The barrier material is a paste formed immediately prior to its use by mixing calcium sulfate powder with any biocompatible, sterile liquid, whereas the graft material is also a paste form comprised of a mixture of water and at least autogenous cancellous bone, DFDBA, autogenous cortical bone chips, or hydroxylapatite.

U.S. Pat. No. 4,619,655 is directed to Plaster of Paris as a bioresorbable scaffold in implants for bone repair. The inventors provide an animal implant composed of a binder lattice or scaffold of Plaster of Paris and a non-bioresorbable calcium material such as calcium phosphate ceramic particles and, in a specific embodiment, the implant may contain an active medicament bound within the plaster. The implant composition of the invention may be preformed into the desired shape or shapes or it may be made up as a dry mix which can be moistened with water just prior to use to provide a fluid or semisolid, injectable formulation which can be injected into the appropriate body space as required for bone reconstruction.

U.S. Pat. No. 4,384,834 is directed to devices for compacting powder into a solid body, comprising a compaction chamber, a moveable support for the powder which extends into the compaction chamber, and means for launching a punch against the powder to form the solid body. The compaction chamber is formed by a block having a conical bore and a conical sleeve having a continuous uncut sidewall moveable within the conical bore to be radially compressed thereby.

U.S. Pat. No. 5,449,481 concerns apparatus and methods for producing a powder compact comprising loading a rubber mold having a cavity shaped according to a desired configuration of the powder compact into a recess formed by a die, in addition to a lower punch inserted into the die. The method steps include filling a cavity of the rubber mold with powder, placing an upper punch in contact with an opposing surface of the die, and pressing the rubber mold filled with powder in a space formed by the die, the lower punch and the upper punch. In specific embodiments, the upper or lower punches are secured.

U.S. Pat. No. 5,762,978 is directed to a batching device having a series of die holes which are fed powder or granular material, upper and lower punches for each die hole, wherein the punches have counterfacing respective working heads, in addition to a rotary turret comprising the die holes, and driving means for adjusting distances between the working heads of the punches. The driving means includes a driving cam for at least one of the punches and filling operation cam means.

U.S. Pat. No. 6,106,267 regards tooling for a press for making an ingestible compression molded product, such as a tablet, from a granular feedstock material wherein the tooling comprises a die having a cylindrical die cavity and an open end for introducing the feedstock, and first and second punches with end faces which compress the feedstock material and which thereby would form the product whose surfaces conform to the end faces of the punches. The tip portion of the first punch is formed of an elastically deformable material so as to undergo deformation upon compression of the feedstock and which includes a wiping ring for wiping the inner surface of the die cavity upon movement of the punch within the die.

U.S. Pat. No. 5,603,880 concerns methods and an apparatus for manufacturing tablets. Plastic polymer film is pressed to form receptacles and filled with a predetermined amount of a powder under a pressurized condition.

U.S. Pat. No. 6,177,125 regards methods for manufacturing coated tablets from tablet cores and coating granulate using a press having at least one compression chamber and a feed device for tablet cores, comprising adding a pasty tablet core to the coating granulate to be compressed and compressing the coating granulate and the tablet cores simultaneously in a single pressing step.

U.S. Pat. No. 5,654,003 is directed to methods of making a solid comestible by forming deformable particles in size from 150 to 2000 microns wherein the particles are compressible in a die and punch tableting machine by subjecting a feedstock comprising a sugar carrier material, wherein the compressed product possesses a rigid structure and has a hard surface which resists penetration and deformation.

U.S. Pat. No. 5,017,122 regards a rotary tablet press for molding tablets through compression of powders and granules having a plurality of dies which rotate around a central axis, multiple upper and lower punches rotatable with the dies, and means for introducing electrically charged lubricant particles onto the tablets.

U.S. Pat. No. 5,158,728 is directed to an apparatus for forming a two-layer tablet having a die table comprising multiple die stations, each die having a cylindrical cavity. The upper punch and lower punch has at least one insert sized and positioned on the upper punch means and lower punch means, respectively, to fit within the die cavity on the die on die table.

Thus, presently available compositions and methods in the art provide no bone graft substitute particles having consistent shapes and whose shapes interrelate in a manner to impart a three-dimensional structure for strength and bone ingrowth. The present invention supplies a long-sought solution in the art by making BGS products or granules, such as demineralized bone matrix, by powder compaction to provide a scaffold structure for ingrowth from the host bone and for the purpose of easy delivery.

SUMMARY OF THE INVENTION

An object of the present invention is to manufacture a BGS shape by compressing or compacting powder or powders; more specifically, by powder compaction, which is a process used primarily in metal and ceramic powder processing.

Another object of the present invention is to use powder compaction to manufacture an allograft (human bone, DBM) bone graft substitute shape.

An additional object of the present invention is to utilize powder compaction to produce a synthetic or ceramic (such as calcium sulfate or calcium phosphate) bone graft substitute shape.

Another object of the present invention is to use powder compaction to produce an allograft, synthetic or ceramic bone graft substitute shape containing bioactive agents (such as antibiotic, BMPs, acids, angiogenic agents and the like).

An additional object of the present invention is to use powder compaction to produce an allograft/synthetic or ceramic composite bone graft substitute shape.

Another object of the present invention is to use powder compaction to produce an allograft/synthetic or ceramic composite bone graft substitute shape containing bioactive agents.

An additional object of the present invention is to use a processing aid (such as stearic acid, magnesium stearate, calcium stearate) or a mix of two or more of these processing aids to produce a JAX™ shape, tablet, or other shape known in the art.

An object of the present invention is a method of manufacturing a shaped bone graft substitute comprising the step of compressing a granulated bone material into the shape. In a specific embodiment, the bone material is an allograft material, a ceramic material, a polymer or combinations thereof. In another specific embodiment, the material further comprises a processing aid composition. In an additional specific embodiment, the processing aid composition is selected from the group consisting of stearic acid, calcium stearate, magnesium stearate, natural polymer, synthetic polymer, sugar and combinations thereof. In a further specific embodiment, the natural polymer is starch, gelatin, or combinations thereof. In another specific embodiment, the synthetic polymer is methylcellulose, sodium carboxymethylcellulose, or hydropropylmethylcellulose. In a further specific embodiment, the sugar is glucose or glycerol. In an additional specific embodiment, the allograft bone material is cortical-cancellous bone. In another specific embodiment, the allograft bone material is demineralized bone matrix. In a further specific embodiment, the shape is a three-dimensional intricate shape. In another specific embodiment, the shape is selected from the group consisting of a jack, a tablet, a strip, a block, a cube, a chip, a pellet, a pill, a lozenge, a sphere, a ring, and combinations thereof In another specific embodiment, the shape is a JAX™ particle. In a further specific embodiment, the shape is a jack, a JAX™, or a ring. In another specific embodiment, the ceramic material is selected from the group consisting of hydroxylapatite, calcium sulphate, alumina, silica, calcium carbonate, calcium phosphate, calcium tartarate, bioactive glass, and combinations thereof. In another specific embodiment, the substitute further comprises a biological agent. In an additional specific embodiment, the biological agent is added to the material prior to the compaction step. In another specific embodiment, the biological agent is added to the bone graft substitute subsequent to the compaction step. In another specific embodiment, the agent is selected from the group consisting of a growth factor, an antibiotic, a strontium salt, a fluoride salt, a magnesium salt, a sodium salt, a bone morphogenetic factor, a chemotherapeutic agent, a pain killer, a bisphosphonate, a bone growth agent, an angiogenic factor, and combinations thereof. In an additional specific embodiment, the growth factor is selected from the group consisting of platelet derived growth factor (PDGF), transforming growth factor b (TGF-b), insulin-related growth factor-I (IGF-I), insulin-related growth factor-II (IGF-II), fibroblast growth factor (FGF), beta-2-microglobulin (BDGF II), bone morphogenetic protein (BMP), and combinations thereof. In an additional specific embodiment, the antibiotic is selected from the group consisting of tetracycline hydrochloride, vancomycin, cephalosporins, and aminoglycocides such as tobramycin, gentamicin, and combinations thereof. In another specific embodiment, the factor is selected from the group consisting of proteins of demineralized bone, demineralized bone matrix (DBM), bone protein (BP), bone morphogenetic protein (BMP), osteonectin, osteocalcin, osteogenin, and combinations thereof. In an additional specific embodiment, the agent is selected from the group consisting of cis-platinum, ifosfamide, methotrexate, doxorubicin hydrochloride, and combinations thereof. In a further specific embodiment, the pain killer is selected from the group consisting of lidocaine hydrochloride, bipivacaine hydrochloride, non-steroidal anti-inflammatory drugs such as ketorolac tromethamine, and combinations thereof. In another specific embodiment, the particles of the material are less than about 10 millimeters in diameter. In a further specific embodiment, the particles of the material are less than about 250$\mu$m in diameter. In another specific embodiment, the particles of the material are in a range of about 50 to 180 microns.

In an additional object of the present invention, there is a method of manufacturing a bone graft substitute comprising the steps of obtaining a bone material; pulverizing the material to produce a granulated bone material; and subjecting the granulated bone material to a powder compaction process. In a specific embodiment, the powder compaction process utilizes a withdrawal press, wherein the press comprises a stationary lower punch; a moveable die; a moveable upper punch; and a moveable lower punch, wherein the stationary lower punch is contained within the moveable lower punch. In a specific embodiment, the powder compaction process utilizes a withdrawal press, wherein the press comprises a stationary lower punch; a moveable lower punch, wherein the stationary lower punch is contained within the moveable lower punch; a stationary upper punch; a moveable upper punch, wherein the stationary upper punch is contained within the moveable lower punch; and a moveable die.

In another object of the present invention there is a method of manufacturing a shaped bone graft substitute from granulated bone material, the method comprising the steps of providing a stationary lower punch and a moveable lower punch which is vertically moveable about the stationary lower punch, a moveable die having at least one cavity and positionable generally above the stationary lower punch, and a moveable upper punch; introducing the granulated bone material into the cavity; positioning the moveable die generally above the stationary lower punch; moving the moveable upper punch to pressably contact the powder in opposition to the moveable lower punch and stationary lower punch; and moving the moveable lower punch to pressably contact the powder in opposition to the moveable upper punch, whereby the moving steps form the material into the shaped bone graft substitute. In a specific embodiment, the steps of moving the upper and lower punches effect a substantially uniform distribution of pressure within the material. In another specific embodiment, the punches are configured such that the shape of the bone graft substitute resulting from the moving steps is a shape selected from the group consisting of a JAX™ particle, a jack, a tablet, a strip, a block, a cube, a pellet, a pill, a lozenge, a sphere, and a ring. In a further specific embodiment, at least one of the moving steps applies a force to the material in a range of about 0.2 to about 5 tons. In another specific embodiment, at least one of the moving steps applies a force to the material in a range of about 0.2 to about 2 tons. In an additional specific embodiment, at least one of the moving steps applies a force to the material in a range of about 0.5 to about 1 ton. In another specific embodiment, the moving step of the moveable lower punch to the material is subsequent to the moving step of the moveable upper punch to the material.

In another object of the present invention there is a method of manufacturing a shaped bone graft substitute from granulated bone material, the method comprising the steps of introducing an amount of the granulated bone material into the cavity; providing a lower punch assembly, an upper punch assembly, and a moveable die positionable generally above the lower punch assembly; positioning the moveable die generally above the lower punch assembly; moving the lower punch assembly in opposition to the moveable upper punch to pressably contact the material; moving the upper punch assembly in opposition to the moveable lower punch to pressably contact the material, whereby the moving steps form the material into the shaped bone graft substitute. In a specific embodiment, the lower punch assembly is comprised of at least one of a stationary lower punch and a moveable lower punch vertically moveable about the stationary lower punch. In another specific embodiment, the upper punch assembly is comprised of at least one of a stationary upper punch and a moveable upper punch vertically moveable about the stationary upper punch.

In an additional specific embodiment of the present invention there is an apparatus for shaping a bone graft substitute from granulated bone material, the apparatus comprising a stationary lower punch having a top surface; a moveable lower punch vertically moveable about the stationary lower punch and having a top surface; a moveable die having at least one cavity and positionable generally above the stationary lower punch; and a moveable upper punch, such that the moveable upper punch moves in opposition to the moveable lower punch to pressably contact the material contained within the cavity, whereupon following pressably contacting the material by the moveable lower punch the top surface height of the lower moveable punch is above the top surface height of the stationary lower punch.

In an additional embodiment of the present invention, there is a method for manufacturing a bone graft substitute from granulated bone material, the method comprising the steps of providing a first punch assembly having a first contact surface configured to effect a relief profile onto a first surface of the granulated bone material; a second punch assembly having a second contact surface; and a moveable die having at least one cavity; introducing the bone material into the cavity; positioning the moveable die generally in alignment with the first punch assembly; moving at least a portion of the first punch assembly to pressably contact the material in opposition to the second punch assembly to effect the desired relief profile on the first surface thereof; and moving at least a portion of the second punch assembly to pressably contact the material in opposition to the first punch assembly, whereby the moving steps form the material into the shaped bone graft substitute.

In another object of the present invention, there is a method for manufacturing a bone graft substitute from demineralized bone matrix material, the method comprising the steps of providing a first punch assembly having a first contact surface configured to effect a relief profile onto a first surface of the demineralized bone matrix material; a second punch assembly having a second contact surface; and a moveable die having at least one cavity; introducing the demineralized bone matrix material into the cavity; positioning the moveable die generally in alignment with the first punch assembly; moving at least a portion of the first punch assembly to pressably contact the material in opposition to the second punch assembly to effect the desired relief profile on the first surface thereof; and moving at least a portion of the second punch assembly to pressably contact the material in opposition to the first punch assembly, whereby the moving steps form the material into the shaped bone graft substitute. In a specific embodiment of the present invention, the contact surface area of the first punch assembly is generally equivalent to a contact surface area of the second punch assembly such that the moving steps apply a substantially uniform pressure distribution to the material. In another specific embodiment, the first punch assembly includes a stationary punch and a moveable punch, such that the steps of moving the first punch assembly includes moving the moveable punch to pressably contact the material. In a further specific embodiment, the second punch assembly includes a stationary punch and a moveable punch, such that the steps of moving the first punch assembly includes moving the moveable punch to pressably contact the material.

In an object of the present invention there is an apparatus for manufacturing a bone graft substitute from a granulated bone material, the apparatus comprising a first punch assembly having a first contact surface having a profile configured to effect a relief profile onto a surface of the bone material; a second punch assembly having a second contact surface, the second contact surface positioned in general alignment with the first contact surface; and a moveable die having at least one cavity, the moveable die being positionable generally in between the first and second punch assemblies.

Other and further objects, features and advantages would be apparent and eventually more readily understood by reading the following specification and by reference to the company drawing forming a part thereof, or any examples of the presently preferred embodiments of the invention are given for the purpose of the disclosure.

DETAILED DESCRIPTION OF THE INVENTION

As used herein the specification, "a" or "an" may mean one or more. As used herein in the claim(s), when used in conjunction with the word "comprising", the words "a" or "an" may mean one or more than one. As used herein "another" may mean at least a second or more.

The present invention is related in subject to the pending application Ser. No. 09/517,981, filed Mar. 3, 2000, and incorporated by reference herein.

I. Definitions

The term "allograft bone material" as used herein is defined as bone tissue that is harvested from another individual of the same species. Allograft tissue may be used in its native state or modified to address the needs of a wide variety of orthopaedic procedures. The vast majority of allograft bone tissue is derived from deceased donors. Bone is about 70% mineral by weight. The remaining 30% is collagen and non collagenous proteins (including bone morphogenic proteins, BMPs). Allograft bone that has been cleaned and prepared for grafting provides a support matrix to conduct bone growth, but is not able to release factors that induce the patient's biology to form bone cells and create new bone tissue. In a preferred embodiment, the allograft is cleaned, sanitized, and inactivated for viral transmission.

The term "biological agent" as used herein is defined as an entity which is added to the bone graft substitute to effect a therapeutic end, such as facilitation of bone ingrowth, prevention of disease, administration of pain relief chemicals, administration of drugs, and the like. Examples of biological agents include antibiotics, growth factors, fibrin, bone morphogenetic factors, bone growth agents, chemotherapeutics, pain killers, bisphosphonates, strontium salt, fluoride salt, magnesium salt, and sodium salt.

The term "bone graft substitute (BGS)" as used herein is defined as an entity for filling spaces in a bone tissue. In specific embodiments, the BGS as used herein is a jack, gel, putty, paste, formable strips, blocks, granules, chips, pellets, tablets, or powder. In a preferred embodiment, the BGS is a shaped particle. In a more preferred embodiment, the shaped particle is a JAX™ particle. In a preferred embodiment, the bone graft substitute is not ingested.

The term "ceramic" as used herein is defined as any non-metallic, non-organic engineering material. An example of such a material is hydroxylapatite, calcium sulphate, alumina, silica, calcium carbonate, calcium phosphate, calcium tartarate, bioactive glass, or combinations thereof.

The term "demineralized bone matrix" as used herein is defined as a bone material which has been treated for removal of minerals within the bone. Examples of demineralization processes known in the art include BioCleanse (Regeneration Technologies, Inc.) or D-MIN (Osteotech, Inc.). In a specific embodiment, the allograft material is subjected to a series of thermal (freezing), irradiation, physical, aseptic, and/or chemical (acid soak) processes known in the art. The latter (acid soak) typically consists of a proprietary permeation treatment to dissolve the minerals contained in the bone. This series of processes combine both demineralization and anti-viral activity.

A skilled artisan recognizes that the actions of bone morphogenic proteins (BMPs) are inactivated by the mineral matrix of the bone. Demineralized bone matrix (DBM) is created from a process that removes the mineral content and allows the bone morphogenic proteins to operate. In addition to removing bone mineral, the processes used to produce DBM also have viral inactivating properties, providing an added assurance of safety for DBM products.

The term "die" as used herein is defined as a tool for imparting a desired shape or form to a material. In a specific embodiment, it is one of a pair of cutting and/or shaping means that when moved toward each other produces a certain desired form in or impresses a desired device on an object by pressure, this tool being the larger of the pair or the part into which the punch enters. In a preferred embodiment, the die is moveable, although in an alternative embodiment the die is stationary. In a preferred embodiment, the die has at least one cavity. In another preferred embodiment, the shape of the cavity of the die is a JAX™ shape and/or facilitates entry of a punch which has an end configured to impart a JAX™ shape onto a material.

The term "granulated bone material" as used herein is defined as a composition comprising particles such as grains, granules, powder, and the like. The particles are preferably comprised of a substance or substances which are amenable for bone growth, bone repair, bone augmentation, and the like. In a specific embodiment, the granulated bone material further comprises a processing aid composition. In a specific embodiment, the mixture is primarily comprised of finely dispersed solid particles. In another specific embodiment, one must view the particles under a microscope to differentiate one particle from another. In a preferred embodiment, it is not a chip. In a specific embodiment, at least the majority of the particles in the mixture are less than about 10 mm in diameter. In a more preferred embodiment, the majority of particles in the mixture are less than about 250 microns in diameter. In a most preferred embodiment, the majority of the particles in the mixture are between about 50 and about 180 microns in diameter.

The term "jack" as used herein is defined as a small object with six arms used in the game jacks. However, in an alternative embodiment, the jack has five arms.

The term "JAX™" as used herein is defined as a bone graft substitute particle which generally has the shape of a toy jack. In a specific embodiment, it is a three-dimensional six-armed star shape.

The term "lower punch assembly" as used herein is defined as an assembly positioned generally below a die and comprised of at least one of a stationary punch and a moveable punch. In a specific embodiment, the stationary punch is an inner punch and the moveable punch is vertically moveable about the stationary inner lower punch.

The term "powder compaction" as used herein is defined as the process wherein a granuluted bone material, such as a powder, is compressed into a desired shape. In a preferred embodiment, the powder is demineralized bone matrix. In another preferred embodiment, the powder particles are less than about 10 mm, more preferably less than about 250 $\mu$m, and most preferably between about 50 and 180 microns in diameter.

The term "pressably contact" as used herein is defined as the touching of a material using pressure upon the material. In a specific embodiment, presssably contacting the material results in compaction of the material, such as in compaction of a granulated bone material, for example a powder.

The term "processing aid composition" as used herein is defined as a composition utilized for facilitating compaction of a powder and release of a compacted powdered product from a die. Specific examples include stearic acid, magnesium stearate, calcium stearate, natural polymer, synthetic polymer, sugar and combinations thereof. In a specific embodiment, the natural polymer is starch, gelatin, or combinations thereof. In another specific embodiment, the synthetic polymer is methylcellulose, sodium carboxymethylcellulose, or hydropropylmethylcellulose. In an additional specific embodiment, the sugar is glucose or glycerol.

The term "pulverize" as used herein is defined as grind, granulate, crush, mash, chop up, or pound a starting material into smaller constituents. In a specific embodiment, the starting material is reduced to powder or dust.

The term "punch" as used herein is defined as an apparatus in the form of a rod, such as comprised of metal or ceramic, that is sharp-edged and variously shaped at one end for imparting a desired shape or form to a material. In a preferred embodiment, the shape imparts a JAX™ shape. In specific embodiments, the punch is solid or hollow.

The term "relief profile" as used herein is defined as a contour on a material having projections and indentations which approximate the contour of the surface which imparts the contour, such as a punch.

The term "substantially uniform distribution of pressure" as used herein is defined as an amount of pressure upon a material which is generally consistent in quantity over the surface of the material.

The term "three-dimensional intricate shape" as used herein is defined as a shape having projections and/or at least one surface that has a relief profile.

The term "upper punch assembly" as used herein is defined as an assembly positioned generally above a die and comprised of at least one of a stationary punch and a moveable punch. In a specific embodiment, the stationary punch is an inner punch and the moveable punch is vertically moveable about the stationary inner upper punch.

The term "withdrawal press" as used herein is defined as a powder compaction press using withdrawal of the die rather than an upper motion of a lower punch for ejection of the product.

II. The Present Invention

A powder compaction process is used to produce a bone graft substitute, such as a JAX™ product comprised of DBM. A processing aid is added to facilitate compaction of the DBM powder and release of the product from the die. A biological agent may also be added to the powder prior to compaction or coated onto the generated product after compaction. The present invention is an improvement over presently available products and methods by taking, in a specific embodiment, an allograft powder, as opposed to a chip, and manufacturing a shape from the powder, wherein the shape is used for a bone graft substitute.

The material from which the BGS is manufactured is a granulated bone material powder, such as an allograft material, a synthetic material, a ceramic material, a polymer, or combinations thereof The allograft material may be processed, such as subjected to a demineralization process, or it may be unprocessed, in which minerals remain intact. The material in any case is preferably cleaned, sanitized, and inactivated for pathogen transmission, such as a virus. The allograft material may be of cortical-cancellous bone or demineralized bone matrix.

In a specific embodiment of the present invention, the bone material is ceramic, such as a calcium salt; calcium sulfate, hydroxylapatite, a calcium phosphate; bioactive glass, a vitreous based glass (such as may be used for maxis-cranio applications); calcium carbonate, a calcium based mineral; various calcium phosphates, and calcium-rich minerals, including tricalcium phosphate and ortho-phosphate; apatite/wollastonite glass ceramic, a calcium silicate often used in bone spacer applications; resorbable polymers such as polysaccharides, polyglycolates, polylactic acid (PLA), polyglycolic acid (PGA), polycaprolactone, polypropylene fumarate (all of which can be blended or made to co-polymers to control the desired properties of the product); and composites of resorbable polymers and glass or ceramic fillers. Bioactive glass is a material whose major components are $CaO$, $SiO_2$ and $P_2O_5$ and whose minor components may be $Na_2O$, $MgO$, $Al_2O_3$ $B_2O_3$ and $CaF_2$.

In a specific embodiment of the present invention, the bone graft substitute is manufactured with a biological agent, either within the substitute particle, coated on the surface of the particle, or both.

In a specific embodiment, the bone material of the present invention is colored to make it more visible. In another specific embodiment, differently shaped BGS of the present invention are denoted with different colors for better differentiation of the particles. In another specific embodiment, the particles are coated or have contained within them an agent such as green fluorescent protein or blue fluorescent protein to make them fluorescent and therefore more visible.

It is preferable for the allograft bone graft substitute embodiment of the present invention to have a granule or shape for easy delivery and scaffold structure. An object of the present invention is providing a BGS which is a shaped particle which may be used as part of a three-dimensional interlocking array of particles. A skilled artisan is aware that the particles may be utilized with inductive graft in which the graft actively facilitates, either directly or indirectly, bone growth. In addition or alternatively, the particles may be utilized for a conductive graft in which the graft is conducive to bone growth but does not actively or directly facilitate it.

The particles will be of an appropriate size such that several individual granules will be used to fill a small void while many can be used to fill larger voids. The three-dimensional structure will allow the granules to fill a volume and, in a specific embodiment, interlock with each other. In another specific embodiment, the particles will be able to interlock with bone. The interlocking will enable the particles to support some mechanical forces while maintaining stability and assist in bone healing. The interlocking feature makes it possible for the particles to resist some shear forces, unlike commercially available products. It will also help to resist migration away from the implant site. The particles will be able to fill odd bone defect shapes and sizes without necessarily needing to carve a larger block to the approximate shape/size. The interlocked particles also provide the ability for the entire implant to behave mechanically more like a single block as compared to current granular products. The shapes would be such that a collection of these particles do not aggregate into a solid, packed volume but instead leave an open, interconnected porosity that is beneficial for bone healing. It is preferred that the shape of the particles and/or the array of the shaped particles allow the engineering or prediction of a specific porosity.

The purpose of having shaped particles is three-fold. First, the capability to interlock provides resistance to shear forces and helps to increase the stability when the graft is packed into a defect. Second, porosity needs to be maintained when the shaped particles are interlocked. It is known in the art that new bone growth can ingress into pores ranging from 100–400 microns in size. The targeted total porosity will range from 20% to 80%, which means that the array of interlocking shaped particles of the invention will retain open spaces of 20–80% of a specific volume of an array. It is important that a graft material provide adequate porosity to allow ingrowth from the host bone. Alternatively, the material must resorb or degrade away to allow for bone replacement. The preferred embodiment is the combination of both of these properties. Third, the shaped particles provide superior handling of BGS product during transfer into the surgical site.

It is an object of the present invention to provide apparatus and methods to manufacture a bone graft substitute through powder compaction of a bone material powder into a shape. Although the bone material powder may be an allograft material, a synthetic material, a ceramic material, a polymer material, or a combination thereof, it is preferably demineralized bone matrix. The shape is preferably one which will provide strength to the bone graft and allow bone ingrowth from the host bone. A preferred shape is a jack, such as a JAX™ particle.

The method of manufacturing the BGS preferably includes compressing, compacting, pressably contacting, packing, squeezing, tamping, or squashing a bone material powder into the desired shape. The method preferably utilizes powder compaction, which a skilled artisan recognizes is a process well known in metal and ceramic powder processing. A processing aid composition is preferably utilized to facilitate compaction of the material and release of the product from the die.

In one embodiment of the present invention, the method includes obtaining a bone material, such as from a donor, cadaver, and the like, pulverizing the material to produce a bone material powder, which a skilled artisan recognizes is preferably to a consistency which is conducive to compaction and generation of a product which is substantially non-friable. The particles are preferably substantially homogeneous in size. The powder is then subjected to a powder compaction process.

The powder compaction process preferably utilizes a withdrawal press. The withdrawal press may comprise a lower punch assembly, an upper punch assembly, and a moveable die. A skilled artisan also recognizes the press will comprise other parts standard in the art, such as a means to fill a die cavity with the powder, and so on. The lower punch assembly may comprise at least one of a stationary punch and a moveable punch; a skilled artisan recognizes this is referred to as a "dual punch". The moveable punch preferably is vertically moveable about the stationary punch. Similarly, an upper punch assembly may comprise at least one of a stationary punch and a moveable punch, wherein the moveable punch preferably is vertically moveable about the stationary punch. In a preferred embodiment, the apparatus comprises a dual lower punch and a stationary upper punch.

The die is preferably moveable, although it may be stationary, and is generally located, during processing, between the lower and upper punch assemblies. It is preferably in alignment with at least one of a lower and upper punch. The die preferably has at least one cavity, and also preferably is shaped corresponding to the desired generated shape of the particle and to permit the corresponding punches to fit in the cavity.

The surfaces of the punches which contact the powder material are preferably configured with a contour or shape that imparts the desired shape onto the powder upon contact with the material. The shape may be a jack, a tablet, a strip, a block, a cube, a pellet, a pill, a lozenge, a sphere, or a ring. The shape of the punches may be that which will impart a jack shape, such as is demonstrated in FIG. 1. The shape is preferably a jack such as a JAX™ particle. In one embodiment of the present invention, one of the punches may impart a jack shape and the other punch may have a generally flat surface, although the resulting product will still result in a jack shape.

In the process, the moveable die and punch assemblies are provided. The powder is introduced into a cavity in the die and the die is positioned generally in alignment with at least one of the punches. In a preferred embodiment, the die is positioned generally above the stationary lower punch. In a specific embodiment, a moveable upper punch pressably contacts the powder in opposition to the moveable lower punch and stationary lower punch. A moveable lower punch moves to pressably contact the powder in opposition to an upper punch. In a specific embodiment, the moving steps occur generally simultaneously, and in other specific embodiments, the moving steps occur in sequence. The steps of moving the upper and lower punches preferably effect a substantially uniform distribution of pressure within the powder. The uniformity of the pressure distribution across the surface of the powder is desirable because it is the best way to ensure the resulting product is structurally sound. The moving steps thus form the powder into the desired shaped BGS.

The moving steps preferably apply a force in the range of about 0.2 to about 5 tons, more preferably about 0.2 to about 2 tons, and most preferably about 0.5 to about 1 ton. The force may be greater, and a skilled artisan recognizes that the upper limit is determined by the critical density of the powder.

In one embodiment of the present invention, there are an apparatus and method for manufacturing a bone graft substitute wherein a stationary lower punch has a top surface, a moveable lower punch vertically moveable about the stationary lower punch has a top surface, and a moveable upper punch, such that when the moveable upper punch moves in opposition to the moveable lower punch to pressably contact the powder in the die cavity the top surface height of the moveable lower punch is above the top surface height of the stationary lower punch.

In one embodiment of the present invention, there is a method for manufacturing a bone graft substitute wherein the steps comprise providing a first punch assembly having a first contact surface configured to effect a relief profile onto a first surface of the bone material powder, preferably a demineralized bone matrix, a second punch assembly having a second contact surface, and a moveable die having at least one cavity; introducing the powder into the cavity; positioning the moveable die generally in alignment with the first punch assembly; moving at least a portion of the first punch assembly to pressably contact the powder in opposition to the second punch assembly to effect the desired relief profile on the first surface thereof, and moving at least a portion of the second punch assembly to pressably contact the powder in opposition to the first punch assembly, whereby the moving steps form the powder into the shaped bone graft substitute.

The contact surface area of the first punch assembly is generally equivalent to a contact surface area of the second punch assembly such that the moving steps apply a substantially uniform pressure distribution to the powder. In a specific embodiment, the first punch assembly includes a stationary punch and a moveable punch, such that the steps of moving the first punch assembly includes moving the moveable punch to pressably contact the powder. In another specific embodiment, the second punch assembly includes a stationary punch and a moveable punch, such that the steps of moving the second punch assembly includes moving the moveable punch to pressably contact the powder.

In another embodiment of the present invention, there is an apparatus for manufacturing a bone graft substitute from a bone material powder wherein the apparatus comprises a first punch assembly having a first contact surface having a profile configured to effect a relief profile onto a surface of the bone material powder; a second punch assembly having a second contact surface, the second contact surface positioned in general alignment with the first contact surface; and a moveable die having at least one cavity, the moveable die being positionable generally in between the first and second punch assemblies.

EXAMPLES

Example 1

Powder Compaction of Demineralized Bone Matrix

Human DBM (HDBM) in powder/chips form was obtained from a bone tissue bank, mechanically ground, and sieved through a #60 mesh (<250μm particle size). Two different batches were processed. Each ground and sieved HDBM was then blended with 2% (in weight) stearic acid, the latter being used as processing aid in the powder compaction process:

|  | HDBM (98%) | Stearic Acid (2%) |
|---|---|---|
| ALLOJAX100-a | 7.6582 g | 0.1562 g |
| ALLOJAX100-b | 19.6 g | 0.4 g |

Figure 1:
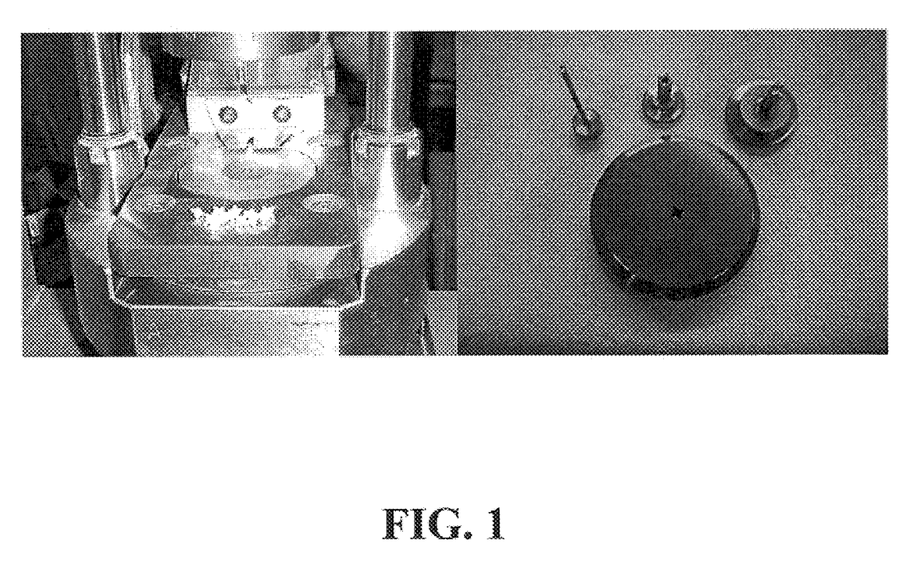
FIG. 1 demonstrates a press configuration used to powder compact JAX™ (left) and die and punches (right).

A powder compaction press (withdrawal type) was used to compress the blends. Special tooling had been made to allow uniform distribution of compressive forces during the compaction process. This involved a one-piece upper punch, two lower punches, and a floating die (FIG. 1). A compression force between 0.6 and 0.7 tons was used.

The powder compaction process is unique to produce bone graft substitutes and bone void fillers. Previous BGS products have been produced using a tableting process. Tablet processing consists of a simple pressing action with a lower punch pressing the powder blend against a stationary, or sometimes translating, upper punch through a stationary die. Tableting typically utilize a tableting press. For more complicated shapes, tableting does not allow for a uniform distribution of pressures within the granules and therefore does not allow for the production of intricate shapes, such as a six-arm JAX™ granule. Powder compaction is an advanced manufacturing process that allows for a uniform distribution of pressures during compaction, therefore allowing for the production of intricate shapes. In addition, specific tooling is required that allows several relative translations between several punches to distribute the compaction pressures. In powder compaction, the upper punch, lower outer punch and die are translating; the lower inner punch is stationary but because of the relative motion of the punches and die, the pressure is evenly distributed within the powder compacted part. Powder compaction requires the use of a withdrawal press. A schematic comparing the tableting to the powder compaction process is shown in FIG. 2.

Figure 2:
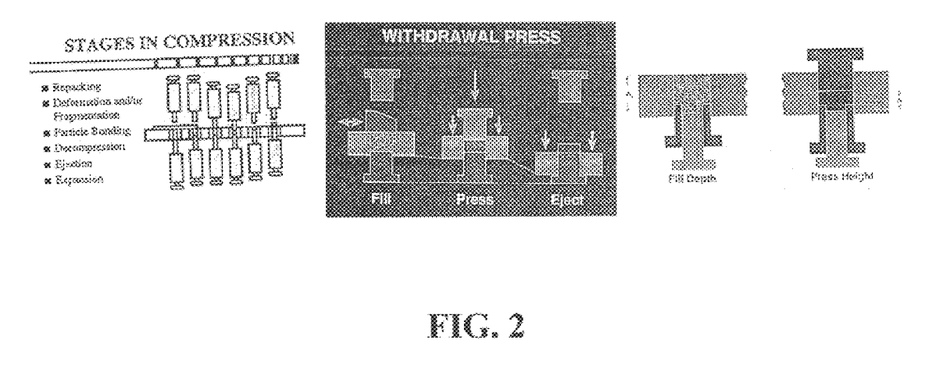
FIG. 2 illustrates a schematic highlighting the differences between (a) conventional tableting and (b, c) the powder compaction used in the novel application to make bone graft substitutes.

FIG. 2 illustrates the differences between (a) conventional tableting and (b, c) the powder compaction used in the novel application to make bone graft substitutes. In (a), the die is stationary, the top and bottom punches are translating; in (b), a withdrawal press is illustrated, in which the lower punch is stationary, the die and upper punch are translating; in (c), an additional lower outer punch allows for a uniform density distribution for an intricate shape, such as JAX™. Thus, a skilled artisan recognizes that a dual lower punch is useful in the present invention. In alternative embodiments, a dual upper punch is utilized wherein the upper punch is composed of an inner punch and an outer punch.

Figure 3:
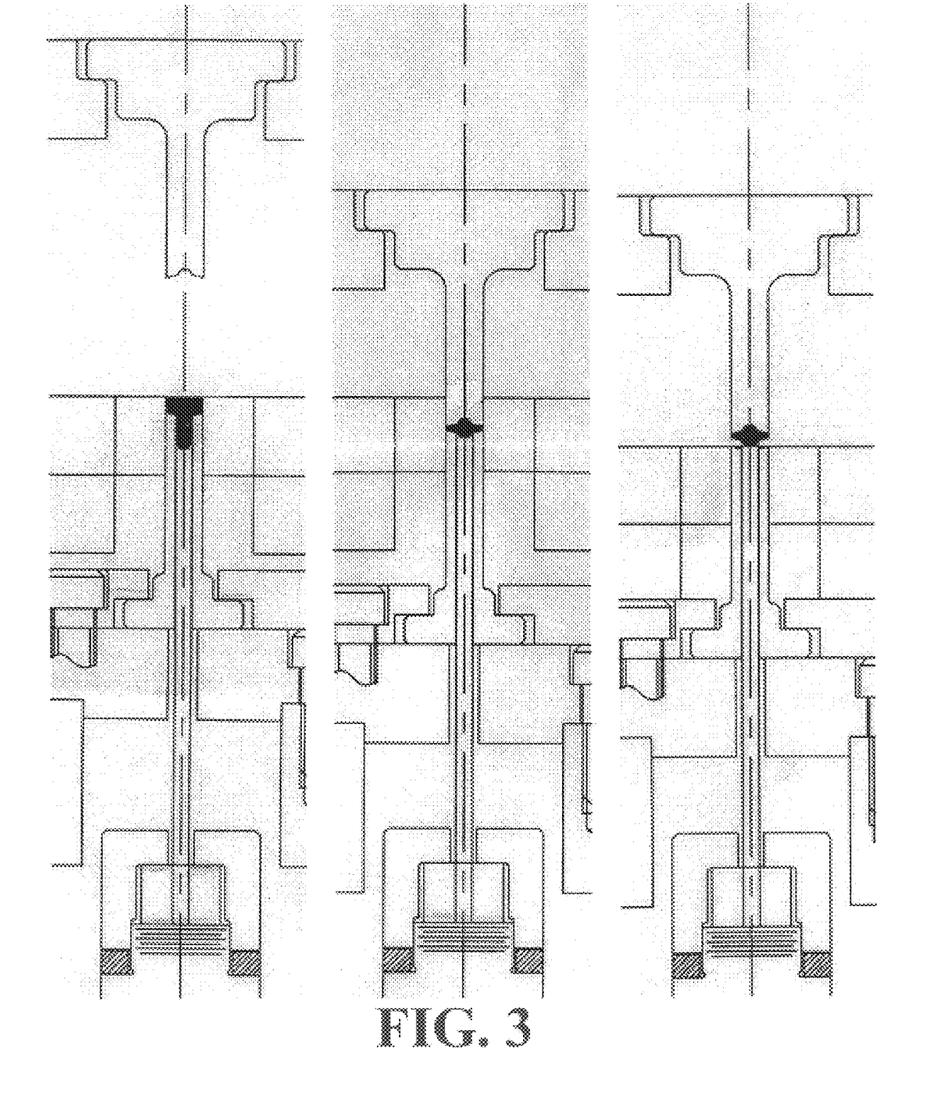
FIG. 3 illustrates powder compaction of a jack shape, wherein (a) is filling of a die cavity, (b) is pressably contacting/compacting the material, and (c) is ejection of the product.

FIG. 3 illustrates a specific embodiment of the present invention, wherein a jack shape is produced through powder compaction. In (a), a die cavity is filled, followed by pressably contacting/compacting the material (b) and ejection of the product (c).

Figure 4:
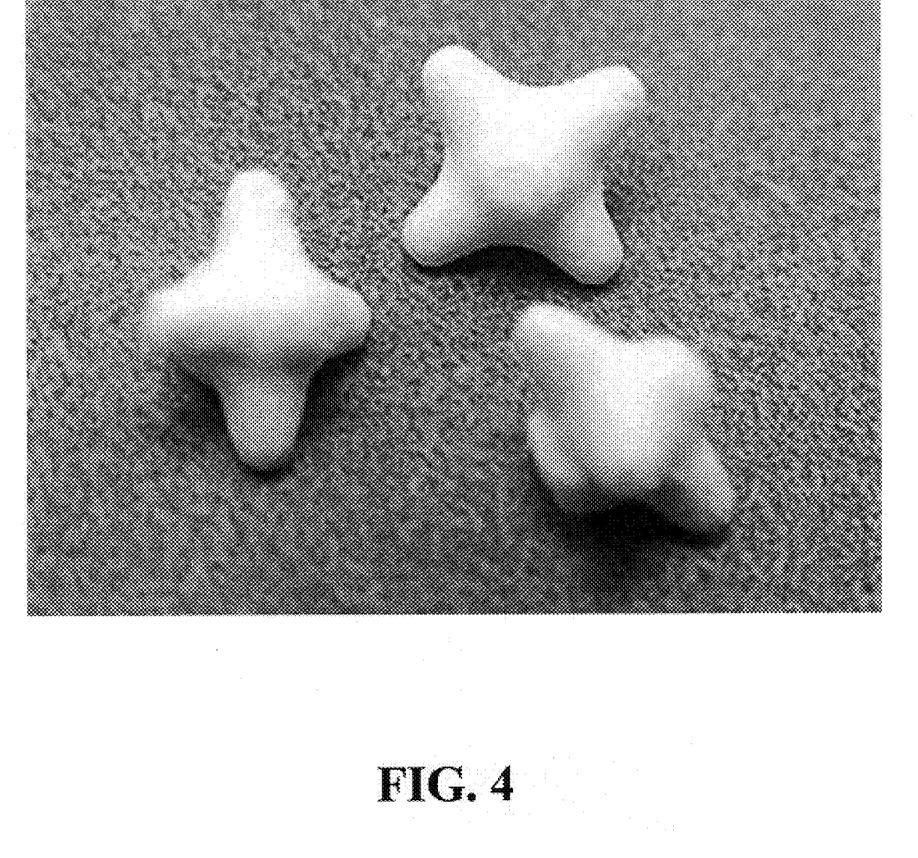
FIG. 4 shows powder-compacted JAX™ manufactured with HDBM (batch # ALLOJAX100-b).

Powder compaction was used to shape DBM powder into an intricate shape (six-arm, JAX™). ALLOJAX100-a compressed poorly; ALLOJAX100-b compressed well and produced a JAX™ product that was not friable between fingers (FIG. 4).

Figure 5:
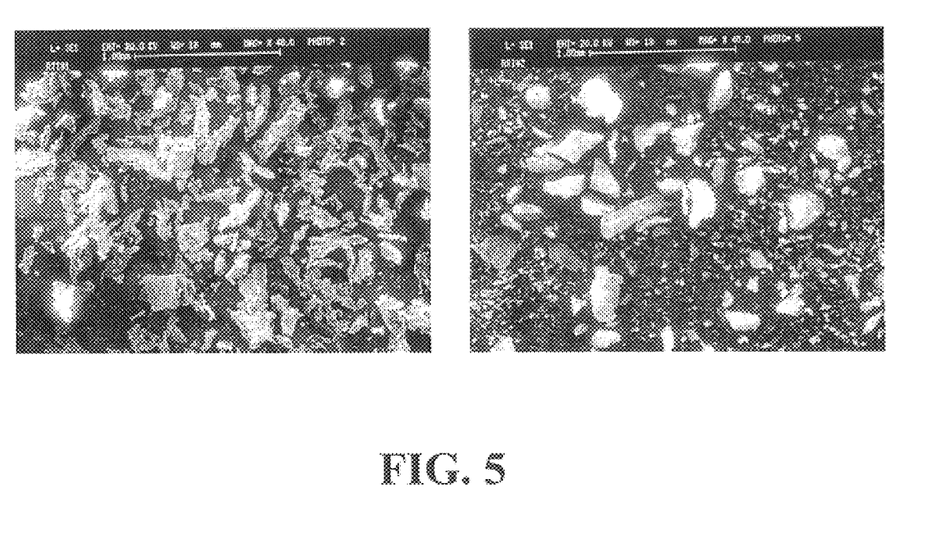
FIG. 5 depicts scanning electron microscopy (SEM) micrographs of HDBM granules: batch #-a (left), batch #-b (right).

Examination of the two blends and two types of HDBM revealed that batch #-a was composed of mostly acicular, elongated particles, probably mainly cancellous bone tissue, while batch #-b was composed of mostly granules and some fines, probably mainly cortical bone tissue (FIG. 5). The morphology of batch #-b is recommended for powder compaction. Density measurements confirmed the difference between the batches: batch #-b was denser (2.0684 g/cm$^3$) than batch #-a (1.3372 g/cm$^3$).

Example 2

Biological Agents

In a preferred embodiment of the present invention, a biological agent is included in the powder or on the generated shape. Examples include antibiotics, growth factors, fibrin, bone morphogenetic factors, bone growth agents, chemotherapeutics, pain killers, bisphosphonates, strontium salt, fluoride salt, magnesium salt, and sodium salt.

In contrast to administering high doses of antibiotic orally to an organism, the present invention allows antibiotics to be included within the composition for a local administration. This reduces the amount of antibiotic required for treatment of or prophalaxis for an infection. Administration of the antibiotic in the BGS would also allow less diffusing of the antibiotic, particularly if the antibiotic is contained within a fibrin matrix. Alternatively, the particles of the present invention may be coated with the antibiotic and/or contained within the particle. Examples of antibiotics are tetracycline hydrochloride, vancomycin, cephalosporins, and aminoglycocides such as tobramycin and gentamicin.

Growth factors may be included in the BGS for a local application to encourage bone growth. Examples of growth factors which may be included are platelet derived growth factor (PDGF), transforming growth factor b (TGF-b), insulin-related growth factor-I (IGF-I), insulin-related growth factor-II (IGF-II), fibroblast growth factor (FGF), beta-2-microglobulin (BDGF II) and bone morphogenetic protein (BMP). The particles of the present invention may be coated with a growth factor and/or contained within the particle or the suspension material.

Bone morphogenetic factors may include growth factors whose activity is specific to osseous tissue including proteins of demineralized bone, or DBM (demineralized bone matrix), and in particular the proteins called BP (bone protein) or BMP (bone morphogenetic protein), which actually contains a plurality of constituents such as osteonectin, osteocalcin and osteogenin. The factors may coat the shaped particles of the present invention and/or may be contained within the particles or the suspension material.

Bone growth agents may be included within the compositions of the present invention in a specific embodiment. For instance, nucleic acid sequences which encode an amino acid sequence, or an amino acid sequence itself may be included in the suspension material of the present invention wherein the amino acid sequence facilitates bone growth or bone healing. As an example, leptin is known to inhibit bone formation (Ducy et al., 2000). Any nucleic acid or amino acid sequence which negatively impacts leptin, a leptin ortholog, or a leptin receptor may be included in the composition. As a specific example, antisense leptin nucleic acid may be transferred within the compositions of the invention to the site of a bone deficiency to inhibit leptin amino acid formation, thereby avoiding any inhibitory effects leptin may have on bone regeneration or growth. Another example is a leptin antagonist or leptin receptor antagonist.

The nucleic acid sequence may be delivered within a nucleic acid vector wherein the vector is contained within a delivery vehicle. An example of such a delivery vehicle is a liposome, a lipid or a cell. In a specific embodiment, the nucleic acid is transferred by carrier-assisted lipofection (Subramanian et al., 1999) to facilitate delivery. In this method, a cationic peptide is attached to an M9 amino acid sequence and the cation binds the negatively charged nucleic acid. Then, M9 binds to a nuclear transport protein, such as transportin, and the entire DNA/protein complex can cross a membrane of a cell.

An amino acid sequence may be delivered within a delivery vehicle. An example of such a delivery vehicle is a liposome. Delivery of an amino acid sequence may utilize a protein transduction domain, an example being the HIV virus TAT protein (Schwarze et al., 1999).

In a preferred embodiment the biological agent of the present invention has high affinity for a fibrin matrix.

In a specific embodiment, the particle of the present invention may contain within it or on it a biological agent which would either elute from the particle as it degrades or through diffusion.

The biological agent may be a pain killer. Examples of such a pain killer are lidocaine hydrochloride, bipivacaine hydrochloride, and non-steroidal anti-inflammatory drugs such as ketorolac tromethamine.

Other biological agents which may be contained on or in the compositions of the present invention are chemotherapeutics such as cis-platinum, ifosfamide, methotrexate and doxorubicin hydrochloride. A skilled artisan is aware which chemotherapeutics would be suitable for a bone malignancy.

Another biological agent which may be included in the BGS of the present invention is a bisphosphonate. Examples of bisphosphonates are alendronate, clodronate, etidronate, ibandronate, (3-amino-1-hydroxypropylidene)-1,1-bisphosphonate (APD), dichloromethylene bisphosphonate, aminobisphosphonatezolendronate and pamidronate.

The biological agent may be either in purified form, partially purified form, commercially available or in a preferred embodiment are recombinant in form. It is preferred to have the agent free of impurities or contaminants.

III. Addition of Fibrinogen to the Composition

It is advantageous to include into the composition of shaped particles any factor or agent which attracts, enhances, or augments bone growth. In a specific embodiment, the composition further includes fibrinogen which, upon cleaving by thrombin, gives fibrin. In a more preferred embodiment, Factor XIII is also included to crosslink fibrin, giving it more structural integrity.

Fibrin is known in the art to cause angiogenesis (growth of blood vessels) and in an embodiment of the present invention acts as an instigator of bone growth. It is preferred to mimic signals which are normally present upon, for instance, breaking of bone to encourage regrowth. It is known that fibrin tends to bind growth factors which facilitate this regrowth.

In an object of the present invention the inclusion of fibrin into the composition is twofold: 1) to encourage bone growth; and 2) to act as a delivery vehicle.

The fibrin matrix is produced by reacting three clotting factors—fibrinogen, thrombin, and Factor XIII. These proteins may be manufactured using recombinant techniques to avoid issues associated with pooled-blood products and autologous products. Currently, the proteins are supplied in a frozen state ready for mixing upon thawing. However, lypholization process development allows that the final product will either be refrigerated or stored at room temperature and reconstituted immediately prior to use. In a preferred embodiment, the clotting factors are recombinant in form.

Only fibrinogen and thrombin are required to produce a fibrin matrix in its simplest form. However, the addition of Factor XIII provides the ability to strengthen the matrix by means of cross linking the fibrin fibrils. Specific mixtures of the three proteins may be provided to generate the appropriate reaction time, degradation rate, and elution rate for the biological agents.

Modifications can be made by altering the fibrin component. One expected modification would be to use hyaluronic acid or a collagen gel instead of or in addition to a fibrin component. Other variations may be inclusion of additional clotting factors in the fibrin matrix. Additional examples of clotting factors are known in the art and may be used, but in a specific embodiment they are clotting factors relevant to a bone disorder. The clotting factors may be purified, partially purified, commercially available, or in recombinant form. In a specific embodiment thrombin alone is used with the patient's own blood or bone marrow aspirate to produce a fibrin matrix.

In a specific embodiment, a biological agent as described above is contained within the fibrin matrix.

Example 3

Alternative Embodiments

Figure 6:
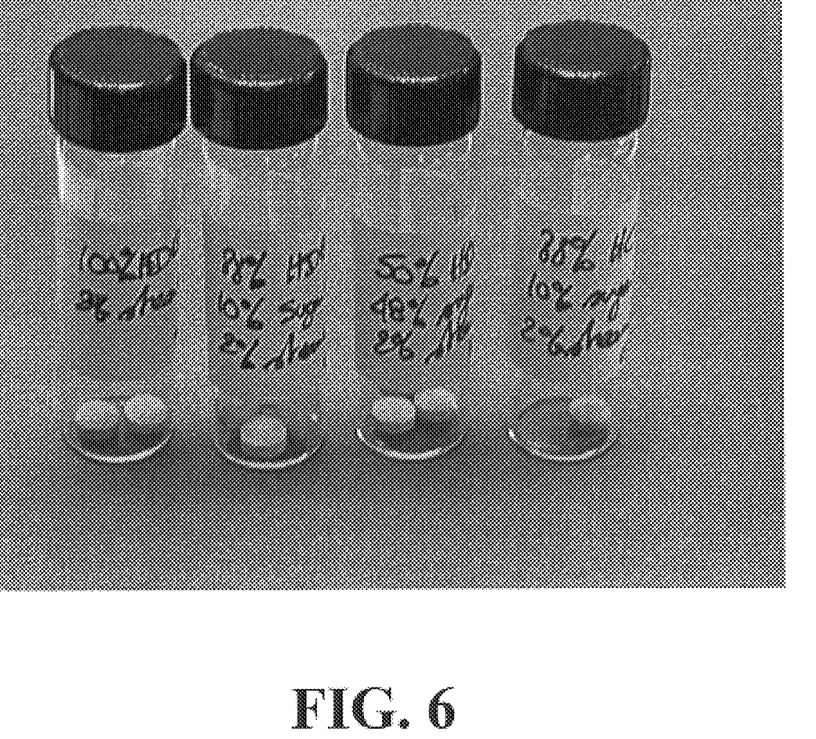
FIG. 6 shows powder-compacted tablets made of 100% HDBM, 90% HDBM+10% calcium sulfate, 50% HDBM+ 50% calcium sulfate and 90% HCC+10% calcium sulfate.

The following blends were successfully compacted into a tablet (about 6 mm in convex shape; FIG. 6):

| Human DBM (%) | Human Corticocancellous Chips (%) | Calcium Sulfate (%) | Fill Weight (mg) | Hardness (Kp) |
|---|---|---|---|---|
| 100 | | 0 | 100 | 5.0–6.7 |
| 90 | | 10 | 120 | 6.1–7.2 |

-continued

| Human DBM (%) | Human Corticocancellous Chips (%) | Calcium Sulfate (%) | Fill Weight (mg) | Hardness (Kp) |
|---|---|---|---|---|
| 50 | | 50 | 120 | — |
| | 90 | 10 | 140 | 2.2–2.4 |
| | 80 | 20 | 140 | 1.6–2.2 |
| | 50 | 50 | 140 | 1.4–1.7 |
| | 90 | 10 | 140 | — |
| | 100 | 0 | 140–170 | — |

For all formulations, the processing aid was stearic acid. The equipment used was a manual hydraulic press, punches used for conventional compression/tableting, and wood blocks for support/guides. Other blends including other allograft (such as human bone or DBM), synthetic or ceramic (such as calcium sulfate or calcium phosphate), or bioactive agents (such as antibiotic, BMPs, acids, and the like), individually or as a mix of two or more of the aforementioned components can potentially be compacted to produce a tablet or a JAX™ shape or other shape. A processing aid, or a blend of two or more processing aids (magnesium stearate, calcium stearate, and stearic acid), may be used in the compaction process.

Example 4

Related Art Embodiments

The following table compares the embodiments of the present invention to those in the related art.

| Category | Product | Manufacturer/Distributor | Comparison to Present Invention |
|---|---|---|---|
| Allograft | Tricortical Strips | American Red Cross Sulzer Spine-Tech Allosource National Tissue Bank | Not processed into shape |
| | Cancellous chips | American Red Cross Allosource National Tissue Bank | Not processed into shape |
| | Cortical/ cancellous chips | American Red Cross Sulzer Spine-Tech Allosource National Tissue Bank | Not processed into shape |
| | Small Implants | Dowels MD-Series (RTI) | Machined from bone |
| DBM | Gel | Grafton (Osteotech) Dynagraft (Gensci Regeneration Laboratories) | Not processed into shape |
| | Putty | Grafton (Osteotech) OrthoBlast, Dynagraft (Gensci Regeneration Laboratories) Allomatrix (Wright Medical Technology) DBX (Synthes) | Not processed into shape |
| | Paste | OrthoBlast (Gensci Regeneration Laboratories) Osteofil (Medtronic Sofamor Danek) DBX (Synthes) Regenafil (RTI) | Not processed into shape |
| | "Crunch" | Grafton (Osteotech) | Not processed into shape |
| | Formable strip | OpteForm (Exactech) Regenaform (RTI) | Thermoplastic/ thermo-formable |

-continued

| Category | Product | Manufacturer/Distributor | Comparison to Present Invention |
|---|---|---|---|
| Bone Substitutes | Blocks, granules/chips (coralline hydroxyapatite) | Pro-Osteon 200, 500 (Interpore) | polymer carrier Harvested from marine coral |
| | Granules/chips (calcium carbonate w/calcium phosphate outer layer) | Pro-Osteon 500R (Interpore) | Harvested from marine coral; patented process (sintering) |
| | Formable strip (bovine collagen with hydroxyapatite and tricalcium phosphate) | Collagraft (Zimmer) | Sintered HA mixed w/collagen on site |
| | Strip (collagen and hydroxyapatite matrix) | Healos (Orquest-non US/ Sulzer Spine-Tech) Healos/MP52 (Orquest-non US/Sulzer Spine-Tech) | Sintered HA coated w/collagen; Impregnated w/BMP |
| | Pellets/tablets (calcium sulfate hemihydrate) | Osteoset (Wright Medical Technology) | Tableted, but may be molded (proprietary information) |
| | Pellets/tablets (calcium sulfate hemihydrate with Tobramycin Sulfate) | Osteoset T (Wright Medical Technology) | Tableted, but may be molded (proprietary information) |
| | Pellets/tablets (calcium sulfate) | Stimulan (Biocomposites/Encore Orthopedics) Profusion (BioGeneration, Inc.) Possibly (Howmedica Osteonics Corp.) | May be molded and/or tableted (proprietary information) |
| | Paste (calcium phosphate) | Alpha-BSM (ETEX-non US) VITOSS Morsels (Orthovita) | May be sintered (proprietary information) |
| | Paste (bioglass/ceramic) | CORTOSS (Orthovita-non US) | Polymer matrix |
| | Porous Blocks (calcium phosphate) | VITOSS (Orthovita) | May be sintered (proprietary information) |
| | Small Implants | RHAKOSS (Orthovita-not commercial) | Unknown-but not compacted (proprietary information) |
| | Gel (fibroblast growth factor and hyaluronic acid) | Ossigel (Orquest) | Not processed into shape |
| | Powder (calcium sulfate) mixed with saline intraoperatively | BonePlast (Interpore) Allo . . . (Wright Medical Technology) | Not processed into shape |

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents

U.S. Pat. No. 4,384,834 issued May 24, 1983.
U.S. Pat. No. 4,619,655 issued Oct. 28, 1986.
U.S. Pat. No. 5,017,122 issued May 21, 1991.
U.S. Pat. No. 5,158,728 issued Oct. 27, 1992.
U.S. Pat. No. 5,366,507 issued Nov. 22, 1994.
U.S. Pat. No. 5,449,481 issued Sep. 12, 1995.
U.S. Pat. No. 5,569,308 issued Oct. 29, 1996.
U.S. Pat. No. 5,603,880 issued Feb. 18, 1997.
U.S. Pat. No. 5,614,206 issued Mar. 25, 1997.
U.S. Pat. No. 5,654,003 issued Aug. 5, 1997.
U.S. Pat. No. 5,762,978 issued Jun. 9, 1998.
U.S. Pat. No. 5,807,567 issued Sep. 15, 1998.
U.S. Pat. No. 6,106,267 issued Aug. 22, 2000.
U.S. Pat. No. 6,030,636 issued Feb. 29, 2001.
U.S. Pat. No. 6,177,125 issued Jan. 23, 2001.

Publications

*Medica Data International, Inc.*, Report #RP-591149, Chapter 3: Applications for Bone Replacement Biomaterials and Biological Bone Growth Factors (2000).

*Orthopaedic Network News*, Vol. 11, No 4, Oct. 2000, pp. 8–10.

One skilled in the art readily appreciates that the present invention is well adapted to carry out the objectives and obtain the ends and advantages mentioned as well as those inherent therein. Particles, compositions, treatments, methods, kits, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of manufacturing a three-dimensional intricately shaped bone graft substitute comprising the step of dry powder compacting a bone material into said three-dimensional intricate shape.

2. The method of claim 1, wherein said bone material is an allograft material, a ceramic material, a polymer or combinations thereof.

3. The method of claim 1, wherein said material further comprises a processing aid composition.

4. The method of claim 3, wherein said processing aid composition is selected from the group consisting of stearic acid, calcium stearate, magnesium stearate, natural polymer, synthetic polymer, sugar, glycerol, and combinations thereof.

5. The method of claim 4, wherein said natural polymer is starch, gelatin, or combinations thereof.

6. The method of claim 4, wherein said synthetic polymer is methylcellulose, sodium carboxymethylcellulose, or hydropropylmethylcellulose.

7. The method of claim 2, wherein said allograft bone material is cortical-cancellous bone.

8. The method of claim 2, wherein said allograft bone material is demineralized bone matrix.

9. The method of claim 2, wherein said ceramic material is selected from the group consisting of hydroxylapatite, calcium sulphate, alumina, silica, calcium carbonate, calcium phosphate, calcium tartarate, bioactive glass, and combinations thereof.

10. The method of claim 1, wherein said substitute further comprises a biological agent.

11. The method of claim 10, wherein said biological agent is added to said material prior to said compaction step.

12. The method of claim 10, wherein said biological agent is added to said bone graft substitute subsequent to said compaction step.

13. The method of claim 10, wherein said agent is selected from the group consisting of a growth factor, an antibiotic, a strontium salt, a fluoride salt, a magnesium salt, a sodium salt, a bone morphogenetic factor, a chemotherapeutic agent, a pain killer, a bisphosphonate, a bone growth agent, an angiogenic factor, and combinations thereof.

14. The method of claim 13, wherein said growth factor is selected from the group consisting of platelet derived growth factor (PDGF), transforming growth factor b (TGF-b), insulin-related growth factor-I (IGF-I), insulin-related growth factor-II (IGF-II), fibroblast growth factor (FGF), beta-2-microglobulin (BDGF II), bone morphogenetic protein (BMP), and combinations thereof.

15. The method of claim 13, wherein said antibiotic is selected from the group consisting of tetracycline hydrochloride, vancomycin, cephalosporins, and aminoglycocides such as tobramycin, gentamicin, and combinations thereof.

16. The method of claim 13, wherein said factor is selected from the group consisting of proteins of demineralized bone, demineralized bone matrix (DBM), bone protein (BP), bone morphogenetic protein (BMP), osteonectin, osteocalcin, osteogenin, and combinations thereof.

17. The method of claim 13, wherein said agent is selected from the group consisting of cis-platinum, ifosfamide, methotrexate, doxorubicin hydrochloride, and combinations thereof.

18. The method of claim 13, wherein said pain killer is selected from the group consisting of lidocaine hydrochloride, bipivacaine hydrochloride, non-steroidal anti-inflammatory drugs such as ketorolac tromethamine, and combinations thereof.

19. The method of claim 1, wherein particles of said material are less than about 10 millimeters in diameter.

20. The method of claim 1, wherein particles of said material are less than about 250 $\mu$m in diameter.

21. The method of claim 1, wherein particles of said material are in a range of about 50 to 180 microns.

22. A method of manufacturing a three-dimensional intricately shaped bone graft substitute comprising the steps of:
   obtaining a bone material;
   granulating said material; and
   subjecting said bone material to a dry powder compaction process; and
   wherein a three-dimensional intricate shape is formed by said dry powder compaction process.

23. The method of claim 22, wherein said dry powder compaction process utilizes a withdrawal press, wherein said press comprises:
   a stationary lower punch;
   a moveable die;
   a moveable upper punch; and
   a moveable lower punch, wherein said stationary lower punch is contained within said moveable lower punch and wherein said moveable lower punch is contained within the moveable die.

24. A method of manufacturing an intricately shaped bone graft substitute from bone material, said method comprising the steps of:
   providing a stationary lower punch and a moveable lower punch which is vertically moveable about the stationary lower punch, a moveable die having at least one cavity that is vertically moveable about the moveable lower punch and positionable generally above the stationary lower punch, and a moveable upper punch that is vertically moveable inside the moveable die;
   positioning the moveable die generally above the stationary lower punch;
   positioning the moveable upper punch generally above the moveable die;
   introducing the granulated bone material into the cavity of the moveable die;
   moving the moveable upper punch to contact the bone material in opposition to the moveable lower punch and stationary lower punch; and
   moving the moveable upper punch further into the cavity of the moveable die, moving the moveable die, and moving the moveable lower punch all at the same time but with different relative amplitudes,
   whereby said moving steps form the material into the intricately shaped bone graft substitute.

25. The method of claim 24, wherein the steps of the relative motions of the upper and lower punches effect a substantially uniform distribution of pressure within said material.

26. The method of claim 24, wherein at least one of the moving steps applies a force to the material in a range of about 0.2 to about 5 tons.

27. The method of claim 24, wherein at least one of the moving steps applies a force to the material in a range of about 0.2 to about 2 tons.

28. The method of claim 24, wherein at least one of the moving steps applies a force to the material in a range of about 0.5 to about 1 ton.

29. The method of claim 24, wherein said moving step of the moveable lower punch to the material is subsequent to the moving step of the moveable upper punch to the material.

30. The method of claim 24, wherein the lower punch is comprised of at least one of a stationary lower punch and a moveable lower punch vertically moveable about the stationary lower punch and moveable inside the cavity of the moveable die.

31. The method of claim 24, wherein the upper punch is comprised of at least one of a stationary upper punch and a moveable upper punch vertically moveable about the stationary upper punch and moveable inside the cavity of the moveable die.

32. The method of claim 1, wherein said shape generally has the shape of a toy jack.

33. The method of claim 1, wherein said shape is a three-dimensional six-armed star shape.

* * * * *